United States Patent
Milliman et al.

(10) Patent No.: US 9,597,080 B2
(45) Date of Patent: Mar. 21, 2017

(54) INSERTION SHROUD FOR SURGICAL INSTRUMENT

(75) Inventors: Keith L. Milliman, Bethel, CT (US); Thomas R. Hessler, Bethel, CT (US)

(73) Assignee: Covidien LP, Mansfield, MA (US)

(*) Notice: Subject to any disclaimer, the term of this patent is extended or adjusted under 35 U.S.C. 154(b) by 2665 days.

(21) Appl. No.: 12/203,245

(22) Filed: Sep. 3, 2008

(65) Prior Publication Data

US 2009/0082789 A1    Mar. 26, 2009

Related U.S. Application Data

(60) Provisional application No. 60/995,026, filed on Sep. 24, 2007.

(51) Int. Cl.
*A61B 17/04* (2006.01)
*A61B 17/115* (2006.01)
*A61B 17/00* (2006.01)
*A61B 17/29* (2006.01)

(52) U.S. Cl.
CPC ............ *A61B 17/115* (2013.01); *A61B 90/00* (2016.02); *A61B 90/08* (2016.02); *A61B 17/1155* (2013.01); *A61B 2017/00336* (2013.01); *A61B 2017/2905* (2013.01); *A61B 2090/08021* (2016.02)

(58) Field of Classification Search
CPC ............ A61B 17/115; A61B 17/1155; A61B 2017/00336; A61B 2017/2905; A61B 2090/08021; A61B 90/00; A61B 90/08
USPC ................. 606/151, 153; 227/175.1
See application file for complete search history.

(56) References Cited

U.S. PATENT DOCUMENTS

| | | |
|---|---|---|
| 4,576,164 A | 3/1986 | Richeson |
| 4,601,710 A | 7/1986 | Moll |
| 4,723,545 A | 2/1988 | Nixon et al. |
| 5,104,025 A * | 4/1992 | Main et al. ............... 227/175.1 |
| 5,350,104 A | 9/1994 | Main et al. |
| 5,355,897 A | 10/1994 | Pietrafitta et al. |
| 5,360,154 A | 11/1994 | Green |
| 5,376,376 A | 12/1994 | Li |
| 5,404,870 A * | 4/1995 | Brinkerhoff et al. ......... 600/184 |
| 5,445,644 A | 8/1995 | Pietrafitta et al. |
| 5,603,698 A | 2/1997 | Roberts et al. |
| 5,902,333 A | 5/1999 | Roberts et al. |
| 5,984,964 A | 11/1999 | Roberts et al. |
| 6,117,148 A | 9/2000 | Ravo et al. |
| 6,149,660 A | 11/2000 | Laufer et al. |

(Continued)

FOREIGN PATENT DOCUMENTS

| | | |
|---|---|---|
| WO | WO 01/21060 | 3/2001 |
| WO | WO 02/00121 | 1/2002 |
| WO | WO 2007/147439 | 12/2007 |

OTHER PUBLICATIONS

European Office Action corresponding to counterpart Int'l Appln. No. EP 08 253 091.6 dated Nov. 17, 2015.

*Primary Examiner* — Gregory Anderson

(57) ABSTRACT

A shroud is provided which includes a rounded atraumatic distal configuration. The shroud is configured and dimensioned to be positioned on the distal end portion of a surgical instrument. The shroud is movable between a first position in which a distal portion of the shroud extends beyond a distal end of a tool assembly of the surgical instrument and a second position in which the distal portion of the shroud is positioned proximal to the distal end of the tool assembly.

11 Claims, 6 Drawing Sheets

(56) References Cited

U.S. PATENT DOCUMENTS

| | | |
|---|---|---|
| 6,193,129 B1 | 2/2001 | Bittner et al. |
| 6,648,900 B2 | 11/2003 | Fleischman et al. |
| 6,648,901 B2 | 11/2003 | Fleischman et al. |
| 6,673,084 B1 | 1/2004 | Peterson et al. |
| 6,702,828 B2 | 3/2004 | Whayne |
| 6,939,328 B2 | 9/2005 | Raulerson |
| 7,090,686 B2 | 8/2006 | Nobles et al. |
| 7,128,748 B2 | 10/2006 | Mooradian et al. |
| 7,402,172 B2 | 7/2008 | Chin et al. |
| 7,744,571 B2 * | 6/2010 | Fisher et al. .............. 604/167.04 |
| 2002/0173809 A1 | 11/2002 | Fleischman et al. |
| 2003/0028178 A1 | 2/2003 | Chin |
| 2003/0144686 A1 | 7/2003 | Martinez et al. |
| 2004/0068278 A1 | 4/2004 | Fleischman et al. |
| 2005/0059996 A1 | 3/2005 | Bauman et al. |
| 2005/0143756 A1 | 6/2005 | Jankowski |
| 2005/0228413 A1 | 10/2005 | Binmoeller et al. |
| 2005/0228446 A1 | 10/2005 | Mooradian et al. |
| 2006/0030877 A1 | 2/2006 | Martinez et al. |
| 2006/0129165 A1 | 6/2006 | Edoga et al. |
| 2006/0229643 A1 | 10/2006 | Nolan et al. |
| 2006/0264986 A1 | 11/2006 | Park et al. |
| 2007/0005084 A1 | 1/2007 | Clague et al. |
| 2007/0021840 A1 | 1/2007 | Lopera |
| 2009/0204108 A1 * | 8/2009 | Steffen .............................. 606/1 |

* cited by examiner

INSERTION SHROUD FOR SURGICAL INSTRUMENT

CROSS-REFERENCE TO RELATED APPLICATIONS

This application claims the benefit of and priority to U.S. Provisional Patent Application No. 60/995,026, filed Sep. 24, 2007, the entire disclosure of which is incorporated by reference herein.

BACKGROUND

Technical Field

The present disclosure relates to a shroud for shielding a surgical instrument, and more particularly, to a shroud for shielding a surgical instrument during delivery of the surgical instrument to a surgical site.

Background of Related Art

A variety of different types of surgical instruments have been developed for manipulating, identifying, treating, repairing and/or excising tissue including organs or portions thereof located within body cavities, such instruments sometimes being hereafter referred to as surgical instruments for treatment of body tissues. These instruments include graspers and fasteners (e.g., staplers, dissectors, biopsy devices, coagulators, etc.). Typically, these instruments are dimensioned to be used in both open and laparoscopic or endoscopic procedures.

In certain surgical procedures for treatment of body tissue, a surgical instrument is inserted through an incision, cannula, or natural orifice to a surgical site where a surgical procedure is to take place. As the surgical instrument is introduced into the surgical site, contaminants (e.g., bowel contents, foreign tissue, etc.) may be picked up by the instrument and brought to the surgical site. Such contaminants may result in harm to the patient by way of infection, or interfere with the surgical procedure. For example, foreign matter may contaminate a wound to cause infection and inhibit healing. Further, foreign matter may interfere with operation of the surgical instrument such as by preventing proper formation of a staple or clip.

Accordingly, it would be useful and beneficial in the art for a device which may be mounted on a surgical instrument for easing insertion of the instrument into a body lumen and for preventing debris and/or contaminants from entering or fouling the instrument during delivery of the instrument to a surgical site.

SUMMARY

In accordance with one aspect of the present disclosure, a surgical instrument comprising a housing, an elongated body portion extending distally from the housing, a tool assembly in mechanical cooperation with a distal end of the elongated body portion, and a shroud positioned on the elongated body portion is disclosed. The shroud preferably has a rounded atraumatic distal configuration. The shroud is movable between a first position and a second position. In the first position, the shroud extends beyond a distal end of the tool assembly. In the second position, a distal portion of the shroud is positioned proximal to the distal end of the tool assembly.

The shroud may include a tab positioned on a proximal end configured to provide a surface for grasping the shroud. The shroud may be made of an elastic material. A central body portion of the shroud may be substantially cylindrical. The distal end of the shroud in one embodiment includes four distal segments which define four slits. The distal segments may be flexible to facilitate movement of the shroud between the first and second positions. The distal segments of the shroud may be configured in a substantially bullet-shaped form.

The tool assembly of the surgical instrument preferably includes a cartridge assembly having a plurality of staple pockets and a portion of the shroud is configured to at least partially cover the plurality of staple pockets. The cartridge assembly may also include a tissue cavity, wherein a portion of the shroud is configured to partially cover the tissue cavity. The shroud may be configured to include an engagement structure, such as a detent, to retain the shroud in the first position.

The shroud may be fabricated from a material selected from the group consisting of moldable and/or thermoformable plastics, polymers, urethanes, natural rubbers, synthetic rubbers, silicones, elastomer and elastomeric materials, latex materials, and sterilizable medical grade material.

In one embodiment, a flange may be formed on an inner surface of the shroud, the flange being positioned to engage a distal end of a surgical instrument when the shroud is in the first position.

The present disclosure also provides a shroud configured for use with a surgical instrument comprising a proximal portion, a distal portion, and a central body portion. The distal portion includes a plurality of distal segments which define a plurality of slits, the distal segments being flexible to facilitate movement of the shroud between the first and second positions. The distal portion defines a rounded atraumatic distal configuration. The shroud is positioned on an elongated body portion of a surgical instrument and is movable between a first position in which a distal portion of the shroud extends beyond a distal end of a tool assembly of the surgical instrument and a second position in which the distal portion of the shroud is positioned proximal to the distal end of the tool assembly.

The present disclosure also provides a shroud for use with a surgical stapling instrument comprising a proximal portion, a distal portion, and a central body portion, the shroud being mountable on an outer surface of the surgical stapling instrument. The distal portion of the shroud is flexible to facilitate movement of the shroud between a first position and a second position with respect to the stapling instrument. At least one tab extends from the shroud which is configured to provide a surface for grasping the shroud.

BRIEF DESCRIPTION OF THE DRAWINGS

Various embodiments of the presently disclosed shroud are described herein with referent to the drawings, wherein.

DETAILED DESCRIPTION

Figure 1:
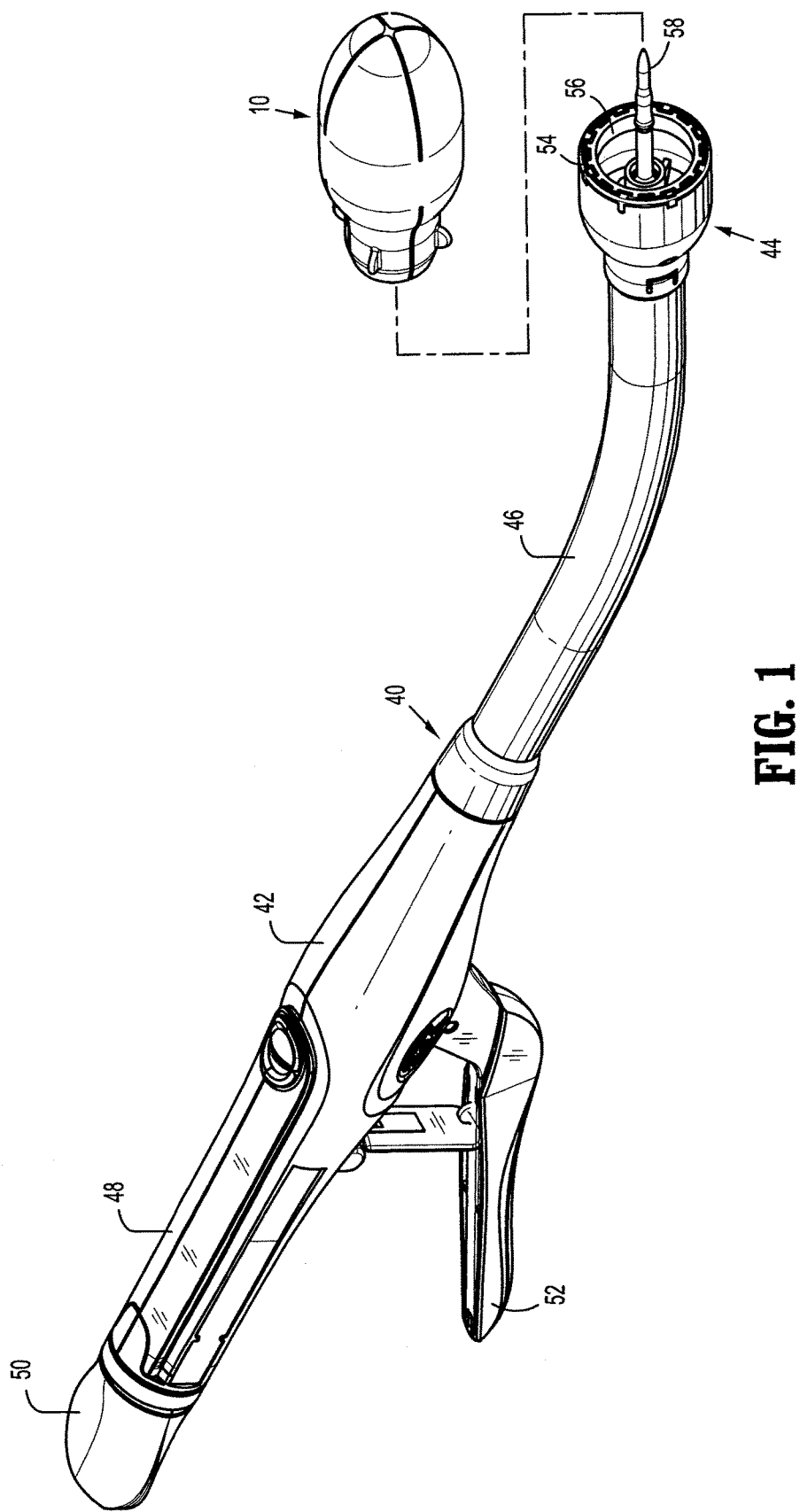
FIG. 1 is a perspective view of a surgical instrument and one embodiment of the presently disclosed shroud with the shroud separated from the surgical instrument.
Figure 2:
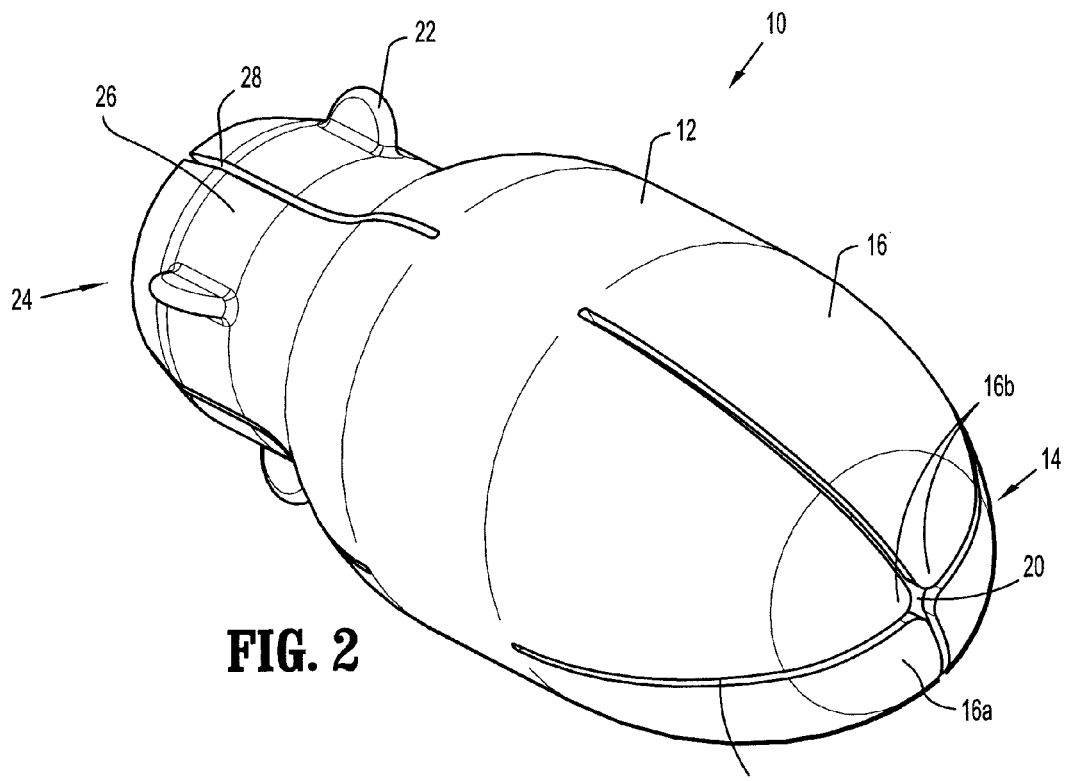
FIG. 2 is a front perspective view of the shroud shown in FIG. 1.

In the present disclosure, it is envisioned that the embodiments discussed may be utilized with and configured for attachment to any endoscopic surgical device having a tool assembly which is suitable for insertion into a body cavity (e.g., circular anastomosis staplers, linear staplers, transverse staplers, open and endoscopic staplers, clip appliers, retractors, surgical forceps, surgical vessel sealers, and the like). It is also envisioned that the embodiments of the present disclosure may be utilized to access various surgical sites via natural orifice openings, or incisions created by surgeons (e.g., mouth, anus, percutaneous incisions, etc.). For purposes of explaining the present disclosure, a circular anastomosis stapler will be the exemplary surgical instrument and the colon will be the exemplary surgical site.

In the drawings and in the description which follows, the term "proximal", as is traditional, will refer to the end of the surgical device or instrument of the present disclosure which is closer to the operator, while the term "distal" will refer to the end of the device or instrument which is further from the operator.

Referring initially to FIG. 1, a surgical instrument is provided which is illustrated as a surgical stapling device 40 having a housing 42, a tool assembly including a cartridge assembly 44 and a shroud 10. Housing 42 includes an approximation knob 50 positioned on the distal end of the handle assembly 48. Handle assembly 48 also includes a firing lever 52 for activating surgical stapler 40 to deploy an arrangement of staples.

Handle assembly 48 is connected to cartridge assembly 44 by an elongated body or endoscopic portion 46. Approximation knob 50 is operatively connected to an anvil retainer 58 in a known manner such that operation, e.g. rotation, of approximation knob 50 effects advancement or retraction of anvil retainer 58. An anvil assembly 59 (shown in FIG. 8) is releasably secured to anvil retainer 58 and is movable into approximation with cartridge assembly 44 by operating, e.g. rotating approximation knob 50. It is also envisioned that anvil assembly 59 may be fixedly connected to device 40.

Cartridge assembly 44 includes two annular arrays of staple pockets 54. Each staple pocket 54 houses a staple (not shown). A tissue cavity 56 defined within cartridge assembly 44 provides a recess for accommodating tissue excised during an anastomosis procedure. A more detailed description of surgical circular anastomosis stapler 40 may be found in U.S. Pat. No. 7,168,604 ("'604 patent"), which is assigned to Tyco Healthcare Group LP. The entire disclosure of the '604 patent is incorporated herein by reference.

Referring to FIGS. 2-5, shroud 10 is formed from a flexible and/or resilient material and has a central body portion 12, a distal end 14, and proximal end 24. The central body portion 12 is preferably substantially cylindrical. Distal end 14 of shroud 10 includes a plurality of distal segments 16, which are positioned adjacent to each other and curve inwardly in a distal direction to define a blunt, substantially bullet-shaped distal end 16a. The tips 16b of the distal segments 16 meet at a distal opening 20. Also, when the distal segments experience load during insertion, they collapse so they cannot expand over the instrument. Although shroud 10 is shown to have four distal segments 16, it is envisioned that shroud may have a different number of distal segments, e.g., two, three, five, etc. Distal segments 16 are spaced apart to define distal slits 18 therebetween. Distal slits 18 allow segments 16 to flex outwardly with respect to each other as will be discussed in further detail below.

Figure 3:
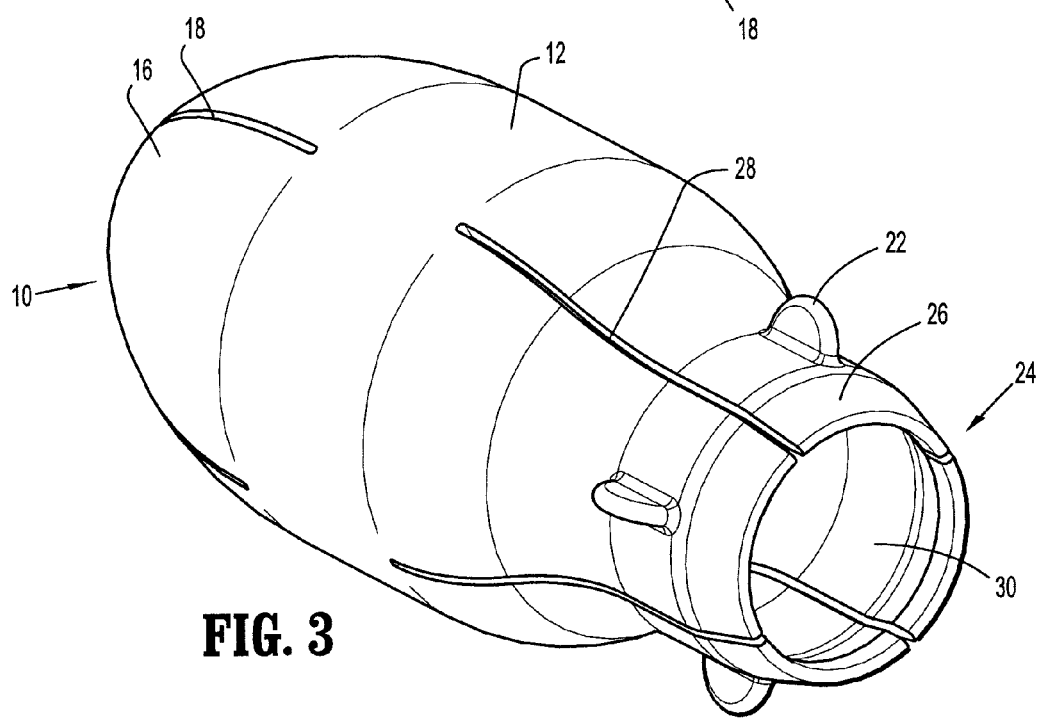
FIG. 3 is a rear perspective view of the shroud shown in FIG. 1.

Proximal end 24 of shroud 10, as shown in FIG. 3, includes tabs 22 on an outer edge of proximal segments 26. Tabs 22 may be molded integrally with shroud 10. Alternatively, tabs 22 can be secured to shroud 10 using any known fastening technique, e.g., welding, soldering, adhesives, screws, etc. Proximal end 24 also includes four proximal segments 26, where the edges of the proximal segments 26 form a circular proximal opening 30 which is dimensioned to be received about the endoscopic body portion of a surgical instrument, e.g., endoscopic body portion of surgical stapler 40. Although shroud 10 is shown to include four proximal segments, it is also envisioned that shroud may have a different number of proximal segments 26. Proximal segments 26 are spaced apart to define slits 28, which allow proximal segments 26 to flex outwardly in relation to each other.

Figure 4:
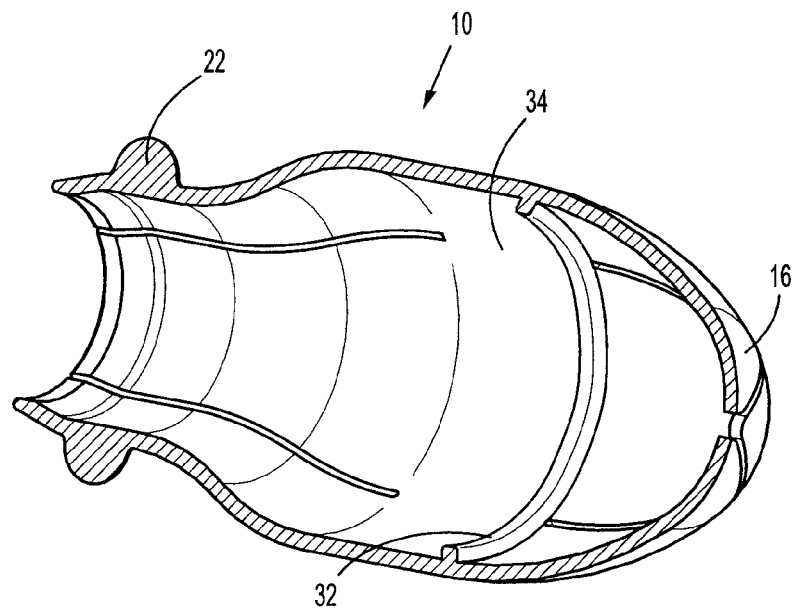
FIG. 4 is a cross-sectional view of the shroud shown in FIG. 1.
Figure 5:
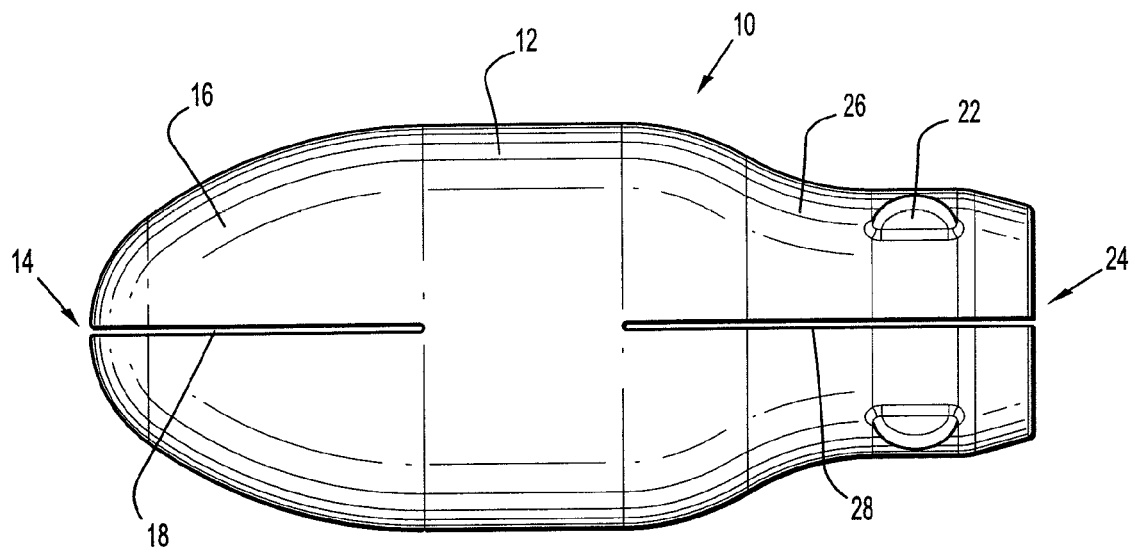
FIG. 5 is a side view of the shroud shown in FIG. 1.

Referring to FIGS. 4 and 5, in one embodiment, a flange 32 is formed around the distal edge of inner cavity 34 of central body portion 12. Flange 32 is positioned to rest on the distal edge of cartridge assembly 44 to prevent undesired proximal movement of shroud 10, i.e. prevent shroud 10 from being unintentionally pushed proximally over cartridge assembly 44 during introduction to the surgical site, but still enable retraction of the shroud when desired. Other engagement structures are also contemplated. As discussed above, the distal end of shroud 10 is substantially bullet shaped. The bullet shaped distal end of shroud 10 facilitates smooth entry and passage of a surgical device into and through a body lumen. The smooth tapered distal end of shroud 10 also functions to deflect debris or foreign matter which might be in the way of the surgical device while the surgical device is being introduced into a body cavity.

Shroud 10 may be constructed from any suitable material or combinations of materials including acceptable sterilizable medical grade material or combinations of materials. For example, shroud 10 may be formed of one or more moldable and/or thermoformable plastics, polymers, urethanes, natural or synthetic rubbers, silicones, elastomer and/or elastomeric or latex materials which is or are sufficiently extendible, expandable, pliable, malleable, ductile, compressible, elastic and/or rubbery to provide for controlled deflection yet have sufficient stiffness for passage through a body lumen. The shroud can be manufactured by an injection molding process, a blow molding process with secondary slit, or other processes.

Figure 6:
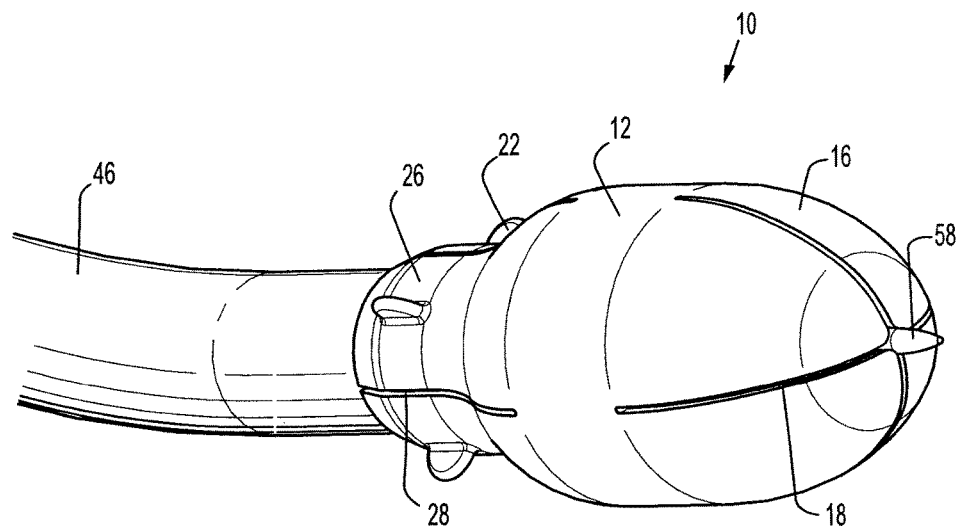
FIG. 6 is perspective view of the shroud shown in FIG. 1 in a first advanced position mounted on the distal end of a surgical instrument.

Referring to FIGS. 5 and 6, in use, shroud 10 is mounted on the distal end of elongated body portion 46 of the surgical stapler 40. Shroud 10 may be mounted by the user by expanding the proximal segments 26 of shroud 10 about the cartridge assembly 44. Alternatively, shroud 10 may be pre-installed about elongated body portion 46 of surgical stapler 40 by the manufacturer prior to attachment of cartridge 46 onto elongated body portion 46.

Figure 7:
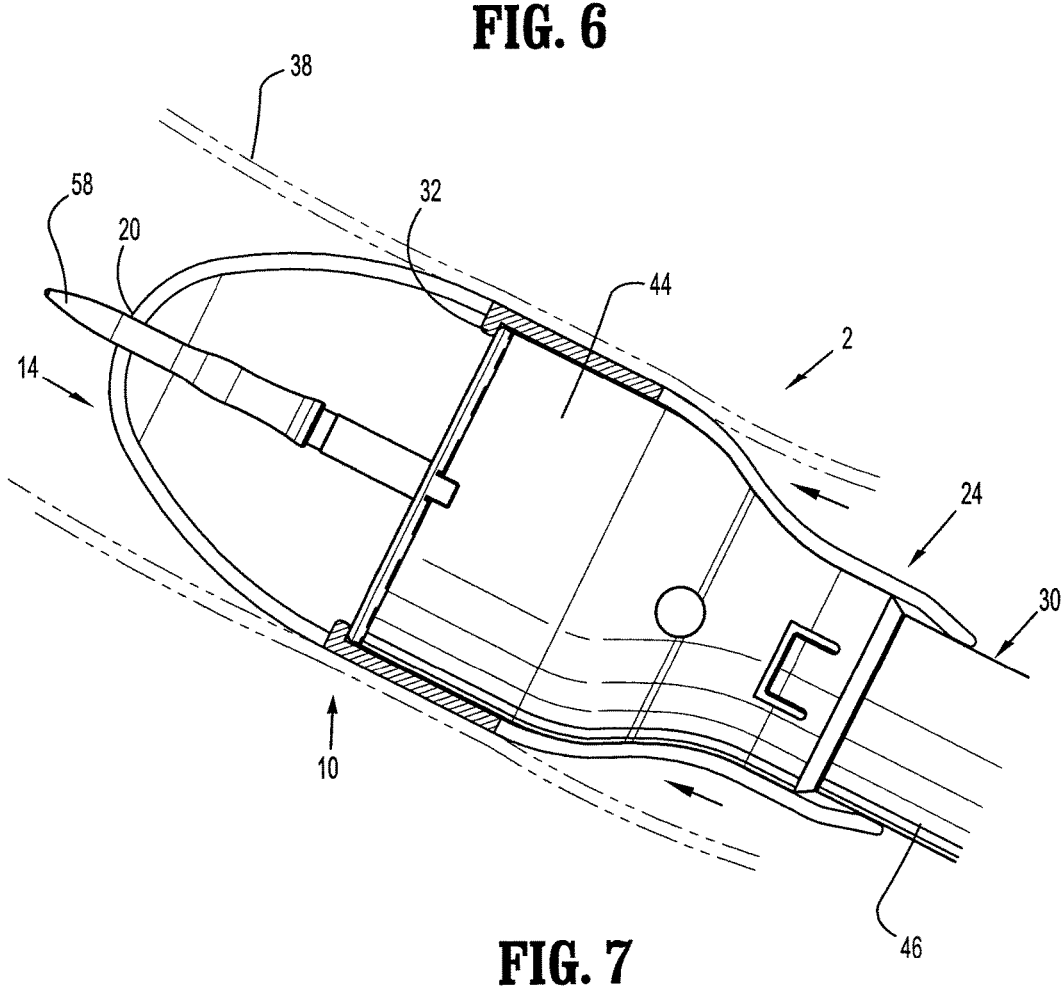
FIG. 7 is a cross-sectional view of the shroud and surgical stapler shown in FIG. 6 positioned within a body lumen.

As depicted in FIGS. 6 and 7, shroud 10 is in a first advanced position, where distal end 14 of shroud 10 extends beyond a distal end of the cartridge assembly 44. Distal segments 16 are formed together such that cartridge assembly 44 is positioned within shroud 10. As illustrated, shroud 10 is configured such that anvil retainer 58 protrudes through opening 20 of shroud. This facilitates attachment of anvil assembly 59 to anvil retainer 58 while shroud 10 is in the advanced position. Also, proximal opening 30 of shroud 10 is positioned about elongated body portion 46.

As illustrated in FIG. 7, elongated body portion 46 is introduced to the surgical site through, for example, colon 38. Elongated body portion 46 is pushed through colon 38 by a user. Flange 32 helps keep shroud 10 in the first position by resting on the cartridge assembly 44 but also enables retraction to the second position when desired. Along the passage through colon 38, there may be some foreign matter or bowel contents that may obstruct the passage of the cartridge assembly 44. The mounted shroud 10 in the first advanced position is configured to deflect and push to the side debris that obstructs the distal end of the shroud 14, thus preventing debris from entering the cartridge assembly 44.

Figure 8:
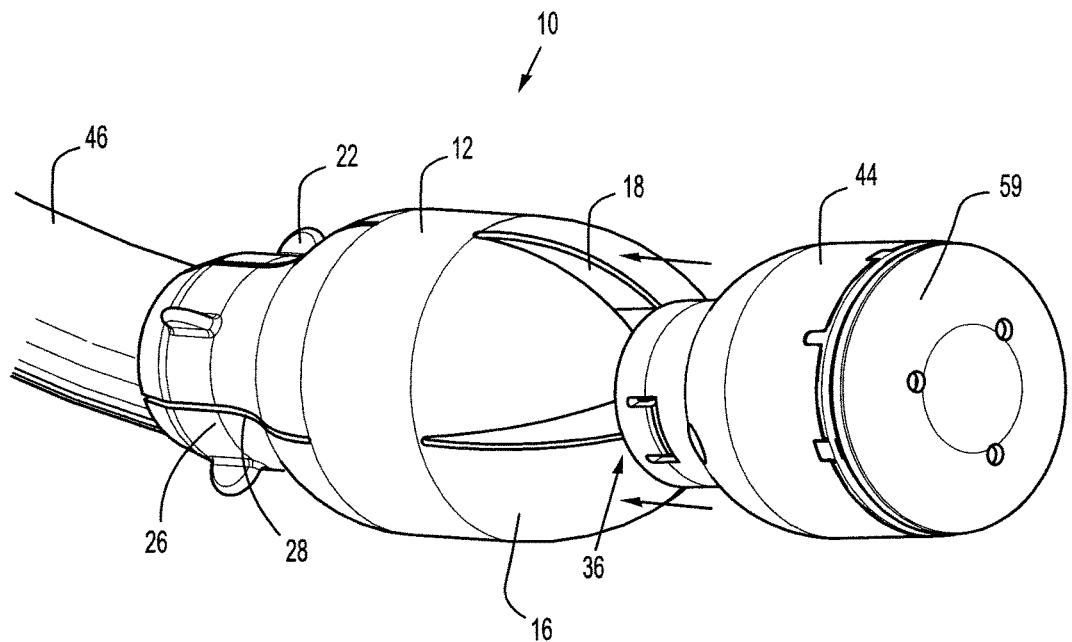
FIG. 8 is a perspective view of the shroud shown in FIG. 1 in a second retracted position mounted on the distal end of a surgical instrument with an anvil assembly attached to the surgical instrument.

FIG. 8 illustrates a perspective view of shroud 10 in a second retracted position on the distal end of elongated body portion 46 with an anvil assembly 59 mounted to the anvil retainer 58 of the stapling device 40. During the surgical procedure, prior to or after the user connects the anvil assembly 59 to the anvil retainer 58, shroud 10 is pulled back to the second position where the distal portion 14 of shroud 10 is proximal to the distal end of the cartridge assembly 44. The user moves shroud 10 into the second position by grasping tabs 22 and pulling shroud 10 proximally back with a surgical tool, for example, a grasper or any other surgical instrument capable of grasping the shroud.

Figure 9:
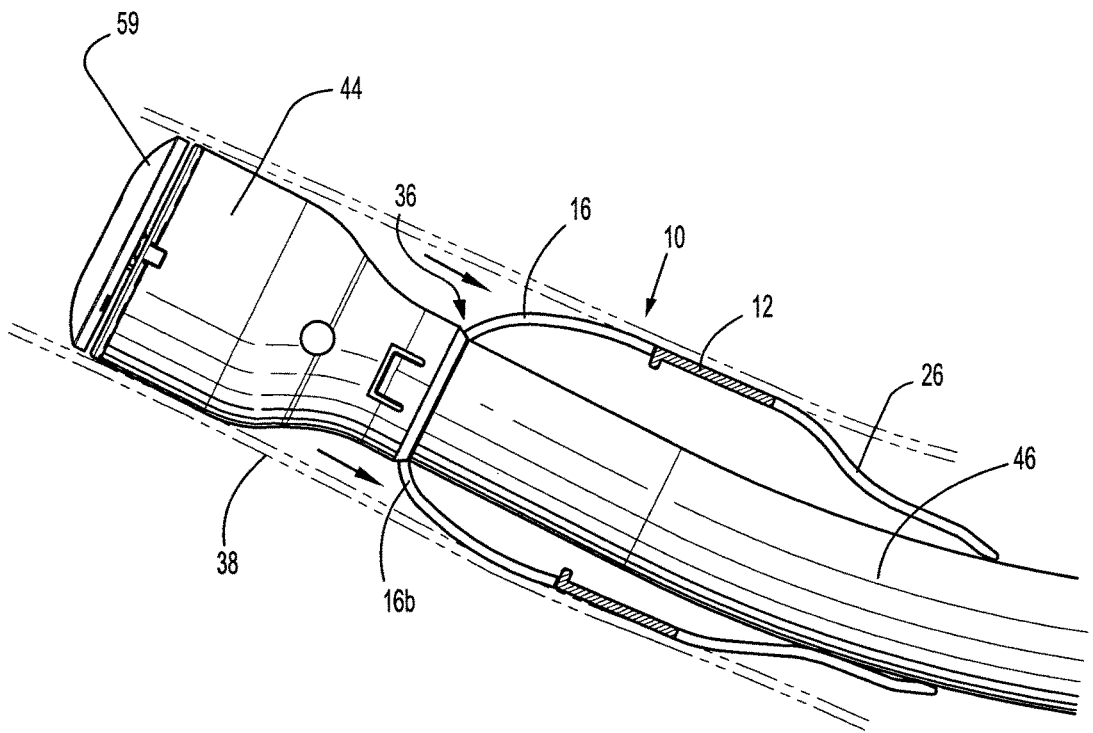
FIG. 9 is a cross-sectional view of the shroud and surgical instrument shown in FIG. 8.

As illustrated in FIG. 9, as shroud 10 is retracted to the second position, distal segments 16 expand outwardly and pass over cartridge assembly 44. In the second position, the distal tips 16b of distal segments 16 and the proximal end 36 of cartridge assembly 44 (which has a smaller diameter than the diameter of the distal end of the cartridge) engage to prevent shroud 10 from moving forward (over the larger diameter region) as the elongated body portion 46 is being removed from the colon 38. Thus, with the shroud 10 not being able to pass over the larger diameter region of the cartridge assembly 44, the shroud is maintained on the instrument during removal.

After the surgical procedure, the user removes the elongated body portion 46, with shroud 10 in the second position.

Figure 10:
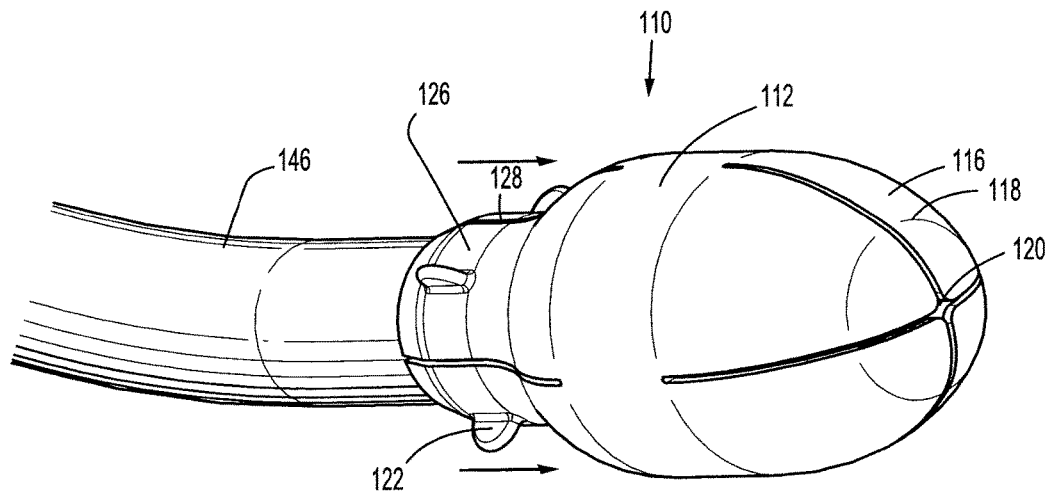
FIG. 10 is a perspective view of the shroud shown in FIG. 1 in a first advanced position mounted on the distal end of a surgical instrument with an anvil assembly secured to the surgical instrument.
Figure 11:
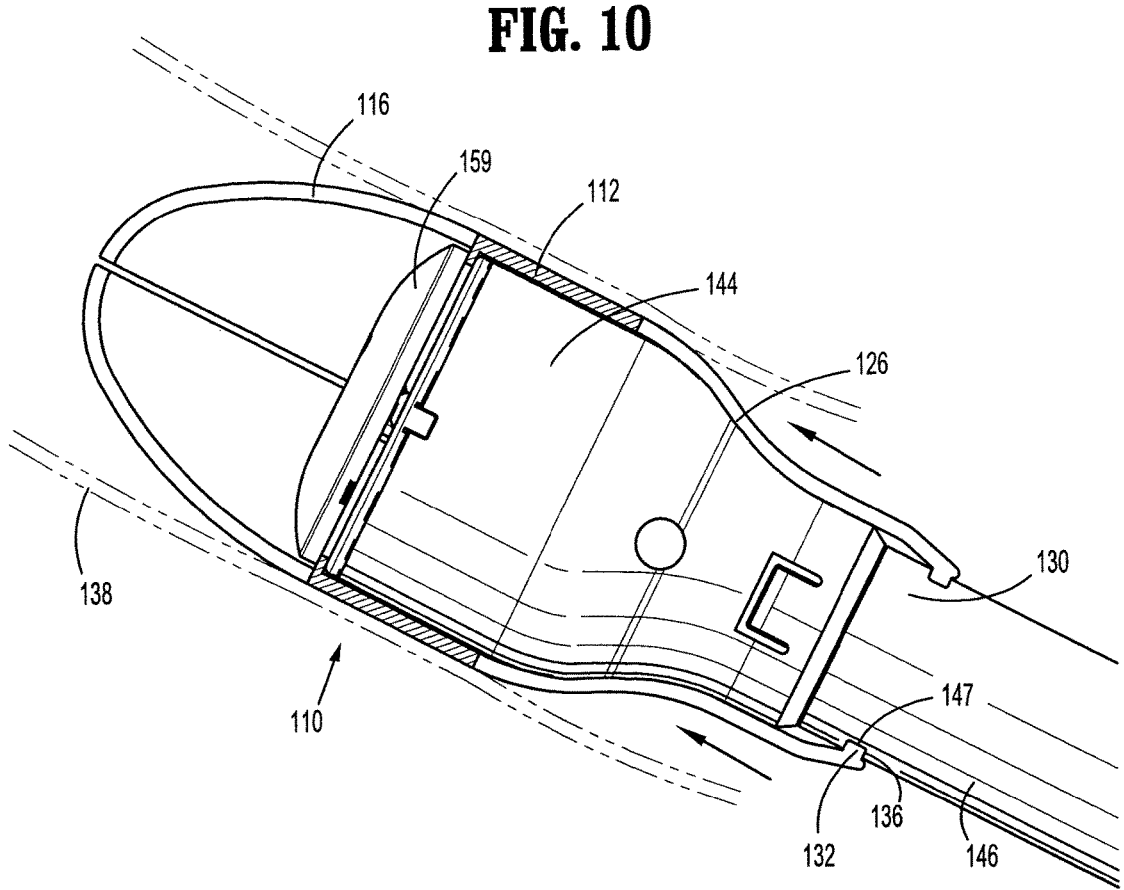
FIG. 11 is a cross-sectional view of the shroud and surgical instrument shown in FIG. 10.

FIGS. 10 and 11 illustrate another embodiment of the presently disclosed shroud shown generally as 110. Shroud 110 is substantially similar to shroud 10 except shroud 110 is dimensioned to enclose cartridge assembly 144 and anvil assembly 159 and has a different engagement structure. As depicted in FIG. 11, endoscopic portion 146 is being introduced into colon 38 with shroud 110 in a first advanced position with anvil assembly 159 installed onto cartridge assembly 144. It is envisioned that anvil assembly 159 may be fixedly attached to endoscopic portion 146.

In this embodiment, shroud 110 is retained in the first advanced position by an engagement structure at interface 136. Interface 136 includes groove 147 which is formed on the distal end of endoscopic portion 146 of a surgical stapler. Groove 147 is configured to extend around at least a portion of the perimeter of endoscopic portion 146. Shroud 10 includes a flange 132 on the inner proximal portion of proximal segments 126. When shroud 10 is in the first position, flange 132 is positioned within groove 147, thus creating a frictional engagement at interface 136. This detent structure thus maintains the shroud in the forward position while also allowing the shroud to be retracted when desired by the user by applying a sufficient force in the proximal direction. Other ways to maintain the shroud are also contemplated.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a housing;
   an elongated body portion extending distally from the housing, the elongated body portion defining a longitudinal axis;
   a tool assembly in mechanical cooperation with a distal end of the elongated body portion; and
   a shroud having a rounded atraumatic distal configuration, the shroud being positioned on the elongated body portion and being movable between a first position in which a distal portion of the shroud extends beyond a distal end of the tool assembly and a second position in which the distal portion of the shroud is positioned proximal to the distal end of the tool assembly, and wherein a proximal end of the shroud is configured for insertion into a body, the shroud including a proximal end, a distal end and a central portion, the distal end including a plurality of distal segments which define a plurality of slits, the distal segments being flexible to facilitate movement of the shroud between the first and second positions, wherein the proximal end of the shroud includes a plurality of flexible proximal segments which define a plurality of slits, the flexible proximal segments being outwardly flexible to facilitate positioning of the shroud on the surgical instrument.

2. A surgical instrument, according to claim 1, further comprising an engagement feature configured to retain the shroud in the first position.

3. A shroud configured for use with a surgical instrument, the shroud comprising:
   a proximal portion, a distal portion, and a central body portion, the distal portion including a plurality of distal segments which define a plurality of slits, the distal segments being flexible to facilitate movement of the shroud between first and second positions, the proximal portion being flexible to enable a diameter of the proximal portion to change during movement of the shroud between the first and second positions, the distal portion defining a rounded atraumatic distal configuration, the shroud being positioned on an elongated body portion of a surgical instrument and being movable between the first position in which a distal portion of the shroud extends beyond a distal end of a tool assembly of the surgical instrument and the second position in which the distal portion of the shroud is positioned proximal to the distal end of the tool assembly.

4. A shroud, according to claim 3, wherein the shroud may be fabricated from a material selected from the group consisting of moldable and/or thermoformable plastics, polymers, urethanes, natural rubbers, synthetic rubbers, silicones, elastomer and elastomeric materials, and latex materials.

5. A shroud, according to claim 3, wherein the shroud may be fabricated from sterilizable medical grade material.

6. A shroud, according to claim 3, further including a flange formed on an inner surface of the shroud, the flange being positioned to engage a distal end of a surgical instrument when the shroud is in the first position.

7. A shroud according to claim 3, wherein the rounded atraumatic distal configuration is configured to be substantially bullet-shaped.

8. A shroud according to claim 3, wherein the distal segments are moved toward a collapsed configuration during insertion of the surgical instrument.

9. A shroud for use with a surgical stapling instrument, the shroud comprising: a proximal portion, a distal portion, and a central body portion, the shroud being mountable on an outer surface of the surgical stapling instrument, the distal portion of the shroud being flexible to facilitate movement of the shroud between first and second positions with respect to the stapling instrument, and at least one tab extending from the shroud, the tab being configured to provide a surface for grasping the shroud, and wherein the at least one tab is configured for insertion into a body, wherein the shroud includes a series of proximal segments forming an opening to receive a portion of the surgical stapling instrument.

10. A shroud according to claim 9, wherein the shroud includes engagement structure to maintain the shroud on the elongated body portion.

11. A surgical instrument, comprising:
a housing;
an elongated body portion extending distally from the housing, the elongated body portion defining a longitudinal axis;
a tool assembly in mechanical cooperation with a distal end of the elongated body portion; and
a shroud having a rounded atraumatic distal configuration, the shroud being positioned on the elongated body portion and being movable between a first position in which a distal portion of the shroud extends beyond a distal end of the tool assembly and a second position in which the distal portion of the shroud is positioned proximal to the distal end of the tool assembly, and wherein a proximal end of the shroud is configured for insertion into a body, wherein the entire shroud is configured for endoscopic insertion into body.

* * * * *